US00PP09727P

United States Patent [19]

Dümmen

[11] Patent Number: Plant 9,727

[45] Date of Patent: Dec. 3, 1996

[54] POINSETTIA PLANT NAMED HWD CAPRI

[75] Inventor: Günter Dümmen, Rheinberg-Eversael, Germany

[73] Assignee: Dummen Jungpflanzenkulturen, Rheinberg-Eversael, Germany

[21] Appl. No.: 516,202

[22] Filed: Aug. 17, 1995

[51] Int. Cl.[6] ..... A01H 5/00

[52] U.S. Cl. ..... Plt./86.4

[58] Field of Search ..... Plt./86.4

*Primary Examiner*—James R. Feyrer

*Attorney, Agent, or Firm*—Proprietary Rights International

[57] ABSTRACT

A new and distinct cultivar of Poinsettia plant named HWD Capri, characterized by its dark red flower bracts; freely branching plant habit; short crop time, early to flower; large, showy cyathia; and excellent postproduction longevity.

1 Drawing Sheet

The present invention relates to a new and distinct cultivar of Poinsettia plant, botanically known as *Euphorbia pulcherrima* Willd., known as the variety Duecap, and hereinafter referred to by the cultivar name HWD Capri.

The new cultivar is a product of a planned breeding program conducted by the inventor in Rheinberg, Germany. The objective of the breeding program was to develop a new dark red variety with good branching and excellent postproduction longevity.

The new cultivar originated from a cross made by the inventor of the cultivar Angelika (U.S. Plant Pat. No. 5,492) as the male or pollen parent with the nonpatented cultivar Steffi as the female or seed parent.

The cultivar HWD Capri was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new Poinsettia are stabilized and reproduced true to type in successive generations of asexual reproduction.

The following traits have been repeatedly observed and are determined to be the unique characteristivcs of HWD Capri. These characteristics in combination distinguish HWD Capri as a new and distinct cultivar:

1. Dark red flowers bracts.
2. Freely branching plant habit.
3. Short crop time, early to flower.
4. Large, showy cyathia.
5. Excellent postproduction longevity.

In comparison to the parent cultivar Steffi, the new Poinsettia has darker red flower bract color; flower bracts have acuminate compared to acute tips; and flower bracts overlap each other whereas the flower bracts of plants of the cultivar Steffi do not overlap giving an open appearance. In comparison to the parent cultivar Angelika, the new Poinsettia has a more red flower bract color; less lobing of the foliage and has longer postproduction longevity as the leaves are retained longer and flower bract color does not fade as quickly.

The accompanying colored photograph illustrates the overall appearance of the new cultivar, showing the colors as true as it is reasonably possible to obtain in colored reproductions of this type. The photograph comprises a top perspective view of a typical potted plant of HWD Capri with one pinched plant in a 15-cm container.

The cultivar HWD Capri has not been observed under all possible environmental conditions. The phenotype may vary somewhat with variations in environment such as temperature, daylength and light intensity, without, however, any variance in genotype. The following observations, measurements and comparisons describe plants grown in Rheinberg, Germany, under commercial practice in a glass-covered greenhouse with day temperatures of 22° C. and night temperatures of 18° C. and light levels of 30,000 to 40,000 lux. Plants were grown in 15-cm pots with one pinched plant per pot.

In the following description, color references are made to the Royal Horticultural Society Colour chart except where general terms of ordinary dictionary significance are used.

Classification:

*Botanical.*—*Euphorbia pulcherrima* Willd.

*Commercial.*—Poinsettia.

*Cultivar.*—*'HWD Capri'*.

Parentage:

*Male parent.*—'Angelika' (U.S. Plant Pat. No. 5,492).

*Female parent.*—*'Steffi'*.

Propagation:

*Type cuttings.*—Terminal cuttings.

*Time to initiate roots.*—Summer: 27° C., 21 days. Winter 20° C., 28 days.

*Rooting habit.*—Fine, freely branching.

Plant description:

*Plant form.*—Vase-shaped.

*Growth habit.*—Freely branching and upright. Branching is enhanced by the removal of the apical shoot tip.

*Foliage description.*—Arrangement: Opposite. Size: Length: 11.5 to 12 cm. Width: 7.5 to 9.5 cm. Shape: Ovate. Tip: Acuminate. Base: Acute. Margin: Lobed. Texture: Upper side: Velvety, glabrous. Under side: Pubescent at veins. Color: Young foliage upper side: 137A. Young foliage under side: Greener than 147B. Mature foliage top side: 137A. Mature foliage under side: Greener than 147B. Venation: Upper side: In between 146B and 144A. Under side: 146B. Petiole: Pattern: Pinnate. Length: 4.5 to 6 cm. Color: 183A.

Flower description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under short day/long night conditions.

*Time to flower.*—8 weeks under short day/long night conditions.

*Quantity of inflorescences.*—10 to 15 cyathia per corymb.

*Inflorescence size.*—Diameter: 28 to 29 cm. Height (depth): 5 to 7 cm.

*Flower bracts.*—Attitude: Horizontal to stem axis. Quantity of flower bracts: 17 per inflorescence. Size: Length: 9 to 11 cm. Width: 5 to 6 cm. Shape: Ovate. Tip: Acuminate. Base: Acute. Margin: Entire, usually not lobed. Texture: Upper side: Satiny, glabrous. Under side: Smooth, glabrous. Color: When opening: 46C then becoming 46B. Mature, top side: Redder than 46B. Mature, under side: 47B. Fading on edges: 38D. Venation: Upper side: 46B. Under side: 47B. Petiole: Length: 14 cm. Color: In between 146A and 146B.

*Cyathia.*—Quantity: 10 to 15 per corymb. Color: Immature: 146C. Mature: 146C. Diameter of cyathia cluster: 4 to 4.5 cm. Stamens: Stamen number: 30 to 40 per cyanthium. Anther size: 0.5 mm. Anther color: 46A. Pollen color: 11A. Pistils: Pistil number: 1 per cyanthium. Stigma color: 183A. Style color: 145C. Style length: 2 mm. Ovary number: 3. Nectaries: Usually one and sometimes two per cyathium.

Disease resistance: No fungal, baceterial nor viral problems observed.

Postproduction longevity: Generally more than 4 weeks under interior conditions.

It is claimed:

1. A new and distinct cultivar of Poinsettia plant named HWD Capri, as illustrated. and described.

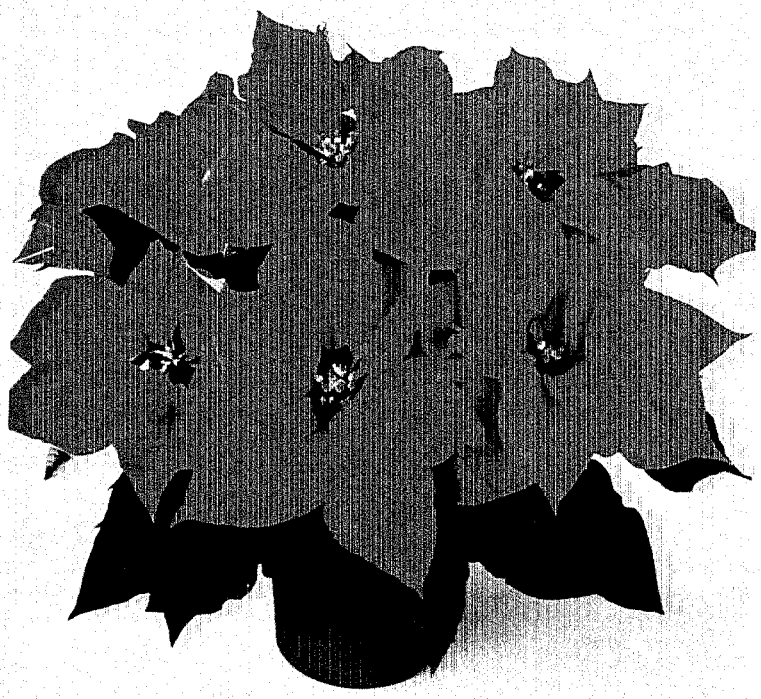

* * * * *